(12) United States Patent
Sealfon et al.

(10) Patent No.: US 10,500,389 B2
(45) Date of Patent: Dec. 10, 2019

(54) SYSTEM AND METHOD FOR FLARED LUER CONNECTOR FOR MEDICAL TUBING

(71) Applicant: REPRO-MED SYSTEMS, INC., Chester, NY (US)

(72) Inventors: Andrew I. Sealfon, Monroe, NY (US); Siavash Gheshmi, Chester, NY (US)

(73) Assignee: Repro-Med Systems, Inc., Chester, NY (US)

( * ) Notice: Subject to any disclaimer, the term of this patent is extended or adjusted under 35 U.S.C. 154(b) by 453 days.

(21) Appl. No.: 15/291,895

(22) Filed: Oct. 12, 2016

(65) Prior Publication Data

US 2017/0189666 A1  Jul. 6, 2017

Related U.S. Application Data

(60) Provisional application No. 62/274,487, filed on Jan. 4, 2016.

(51) Int. Cl.
*A61M 39/10* (2006.01)
*A61M 5/145* (2006.01)

(52) U.S. Cl.
CPC ...... *A61M 39/1011* (2013.01); *A61M 5/1452* (2013.01); *A61M 2039/1033* (2013.01); *A61M 2205/586* (2013.01); *A61M 2205/75* (2013.01)

(58) Field of Classification Search
CPC .... A61M 2039/1033; A61M 2205/586; A61M 2205/75; A61M 39/1011; A61M 5/1452
See application file for complete search history.

(56) References Cited

U.S. PATENT DOCUMENTS

| 4,639,019 A | 1/1987 | Mittleman |
| 5,741,227 A | 4/1998 | Sealfon |
| 5,851,201 A | 12/1998 | Ritger et al. |
| 5,984,373 A | 11/1999 | Fitoussi et al. |

(Continued)

OTHER PUBLICATIONS

PCT International Search Report for International Application PCT/US2016/058056, search report dated Feb. 16, 2017 (Feb. 16, 2017).

*Primary Examiner* — Brandy S Lee
(74) *Attorney, Agent, or Firm* — Daniel W. Roberts; Law Offices of Daniel W. Roberts, LLC

(57) ABSTRACT

Provided is a system and method for a flared luer connector for medical tubing. More specifically, the flared luer connector includes a tube head adapter formed of a resilient material providing an inlet and opposite thereto an outlet with a longitudinal axis there between. A luer lock fitting is formed proximate to the inlet and structured and arranged to engage a syringe, and at least one flared member disposed between the luer lock fitting and the outlet, the flared member rising from the tube head adapter and angled towards the outlet. The flared member also provides at least one engaging surface between the tube head adapter and a distal edge, the engaging surface acutely angled with respect to the longitudinal axis. The engaging surface is structured and arranged to engage with a corresponding receiving section of a base, the base having a deflector section structured and arranged to deflect a tube head adapter having other than the corresponding flared member. An associated method of use is also provided.

68 Claims, 12 Drawing Sheets

(56) References Cited

U.S. PATENT DOCUMENTS

| | | |
|---|---|---|
| 6,170,800 B1 | 1/2001 | Meloul et al. |
| 7,641,620 B2 | 1/2010 | Winger |
| 7,857,802 B2 | 12/2010 | Brandenburger et al. |
| 8,731,638 B2 | 5/2014 | Butler et al. |
| 8,746,745 B2 | 6/2014 | Colman |
| 9,017,291 B2 | 4/2015 | Delabie |
| 2002/0147429 A1* | 10/2002 | Cowan ............... A61M 39/1011 604/187 |
| 2008/0140055 A1 | 6/2008 | Shirley |
| 2015/0080814 A1* | 3/2015 | Lambert ............. A61M 39/105 604/250 |

* cited by examiner

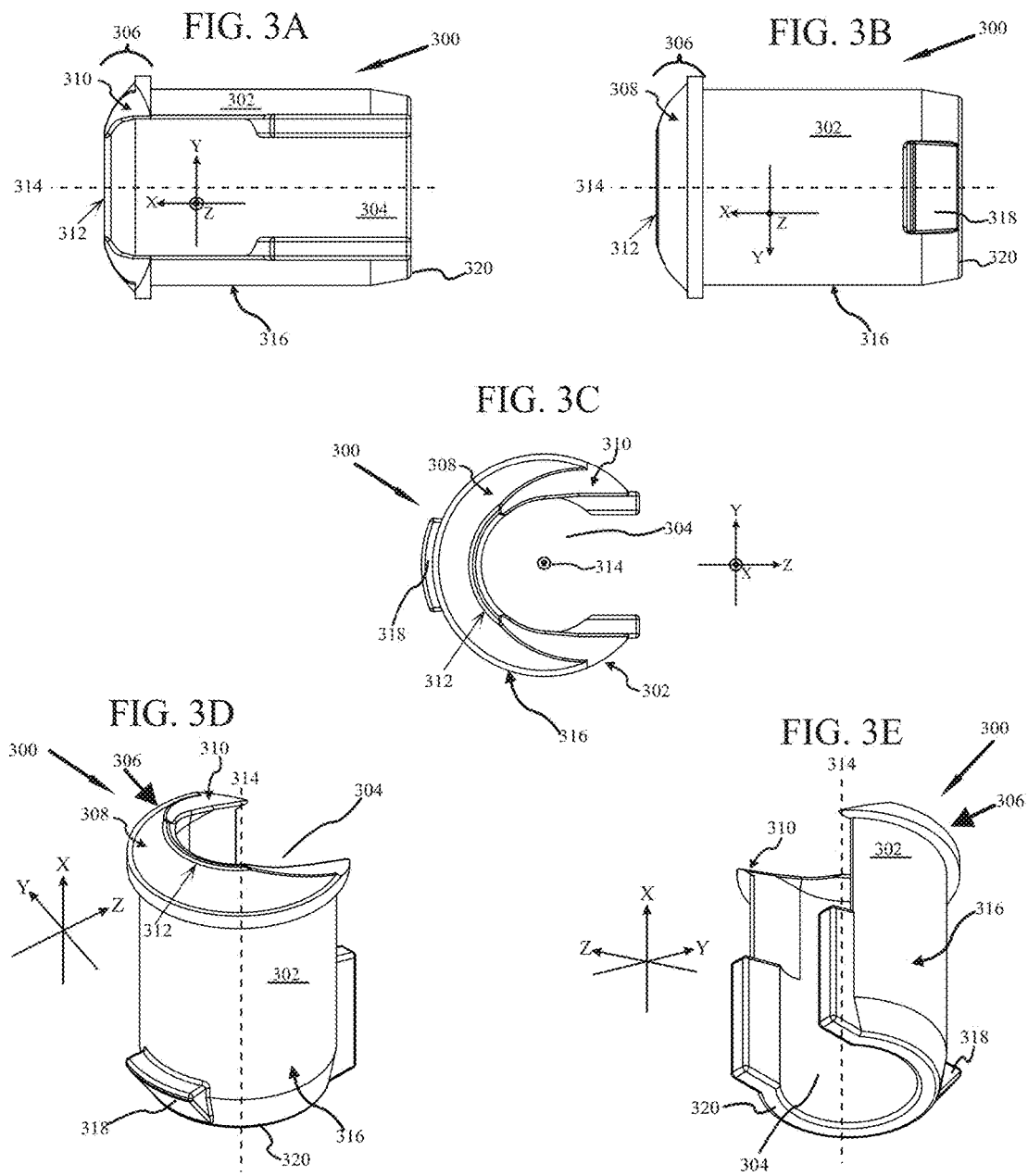

FIG. 7
FIG. 8
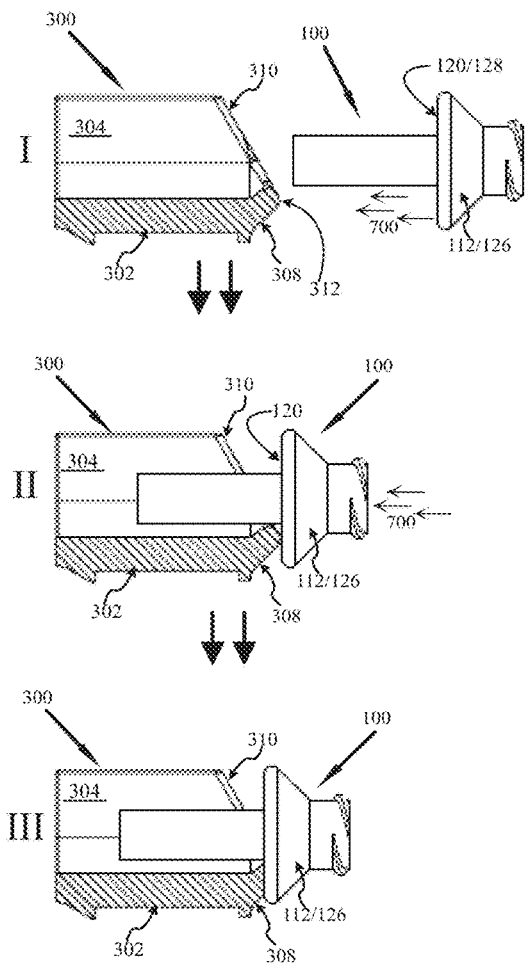
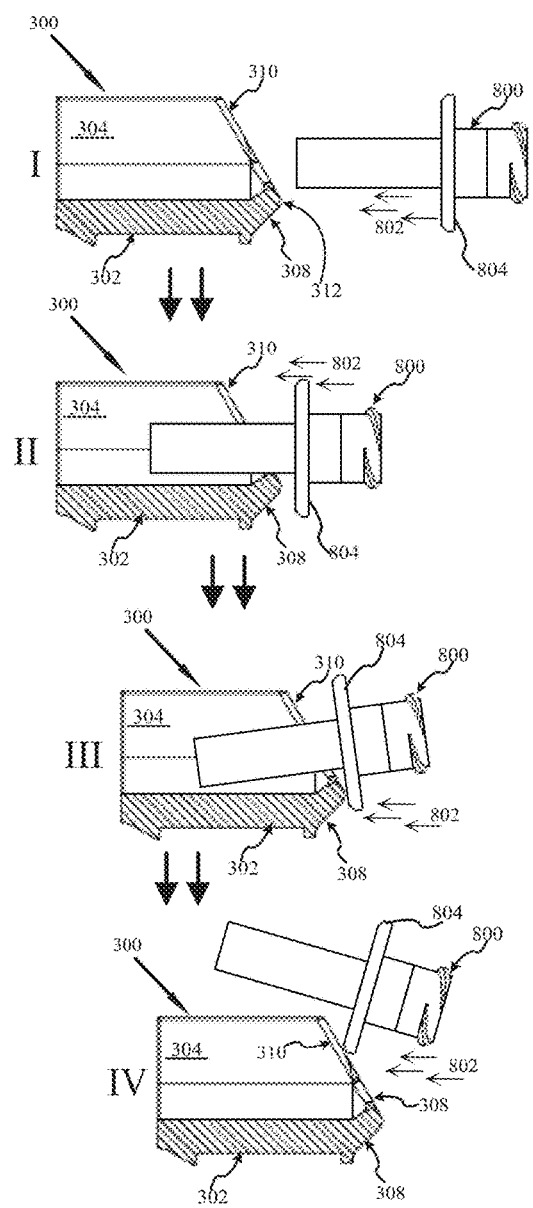

FIG. 10A
FIG. 10B
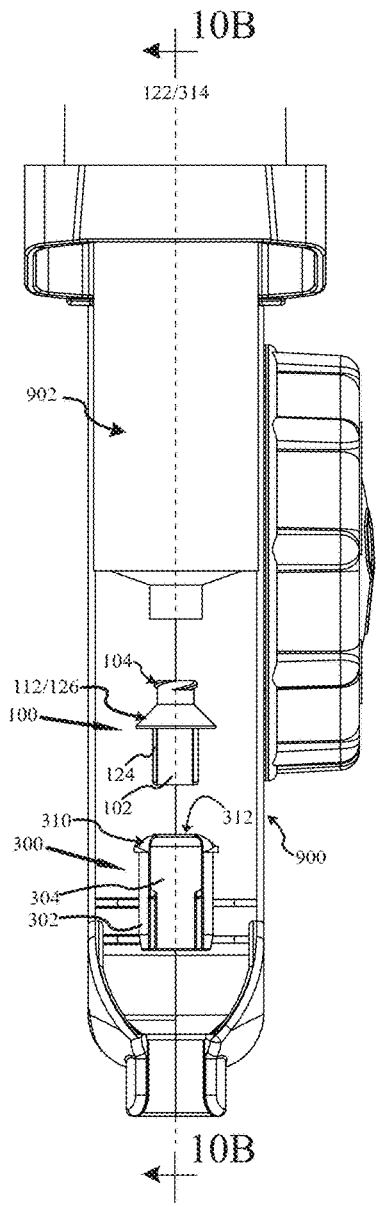
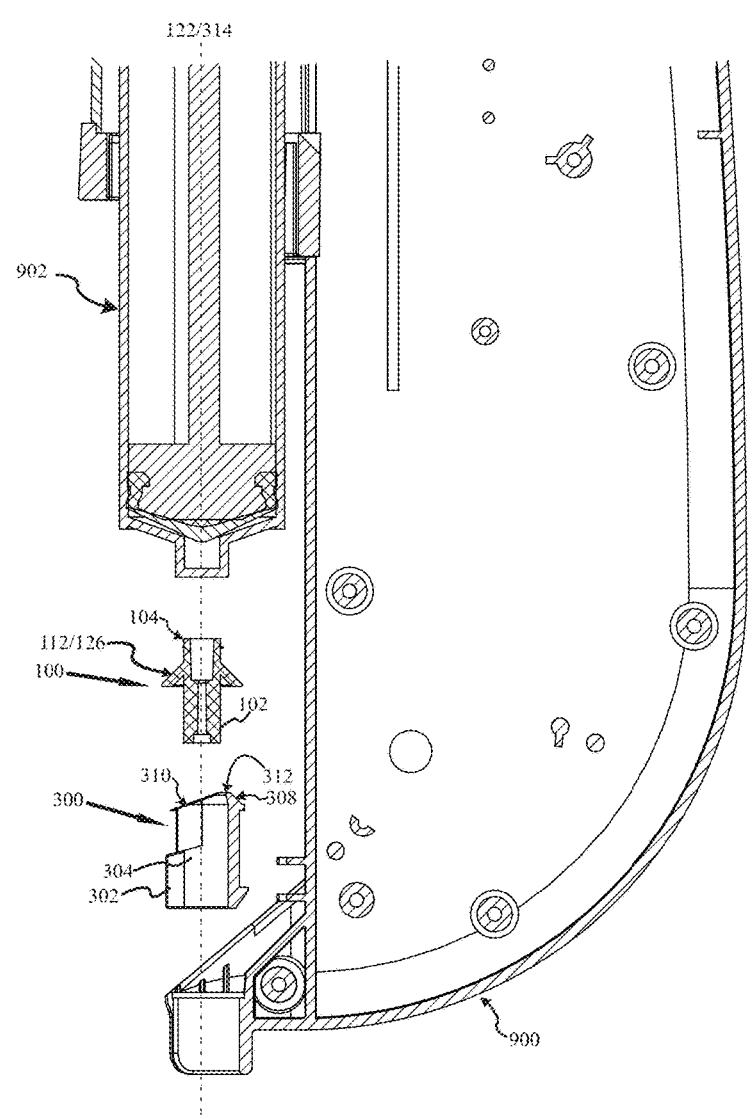

SYSTEM AND METHOD FOR FLARED LUER CONNECTOR FOR MEDICAL TUBING

CROSS REFERENCE TO RELATED APPLICATIONS

This application claims the benefit under 35 U.S.C. § 119(e) of U.S. Provisional Application No. 62/274,487 filed Jan. 4, 2016 and entitled SYSTEM AND METHOD FOR FLARED LUER CONNECTOR FOR MEDICAL TUBING, the disclosure of which is incorporated herein by reference.

FIELD OF THE INVENTION

The present invention relates generally to medical devices, and more specifically to medical tubing and systems and methods of maintaining sterility and eliminating the opportunity for random inter connection between tubing and a syringe by ensuring proper connections to syringes or other pharmaceutical reservoirs and pumps for the delivery of pharmaceutical products. In addition, the present invention minimizes the opportunity for use of third party or unintended medical tubing by employing a specific coupling system.

BACKGROUND

Liquid pharmaceuticals are commonly delivered to patients through injection or infusion. Such delivery is generally made in one of two ways. The first is an immediate delivery from a health care provider in the form of a simple injection performed with a syringe and a needle directly disposed to the tissue of the patient. The second is gradual delivery, wherein a syringe or other reservoir is connected to specific medical tubing for delivery over time.

Frequently, syringe pumping systems such as Sealfon U.S. Pat. No. 5,741,227 teaching a Method of Sterile Preparation of IV Pump Syringe are used. As noted, Sealfon teaches a number of advantages for maintaining the sterility of the tubing set 14, coupling the tubing set 14 to the syringe 12, and disposing the coupled syringe 12 within a syringe pump 10.

More specifically, Sealfon teaches a disc 48 that is added to the tubing set 14 at the connector end interposed between the tubing set per se inlet 34 and a tubing engaging means 50. This disc 48 has been shown to provide and perform many advantages. For example, this disc 48 serves to elevate the tubing end from surfaces, thereby promoting the sterile condition of the tubing end, if and/or when it is set down when unconnected to a syringe.

In addition, the disc 48 provides a convenient brace for an operator's fingers during the coupling of the tubing set to a syringe—the disc 48 further preventing slippage of the fingers over the inlet 34 that again promotes sterility of the inlet 34. And further still, the disc provides a brace for the syringe pump 10, ensuring that when the coupled syringe 12 and tubing set 14 are disposed within the syringe pump 10, the disc 48 provides a brace against which the force of the syringe pump 10 serves to temporarily lock the coupled syringe 12 and tubing set 14 in place.

By using calibrated tubing and needles together with a constant pressure pump, such as the Sealfon '227 syringe pump, it is possible to virtually guarantee safe delivery of a liquid to tissue. When saturation of the tissue occurs the resistance to the flow increases and the system immediately self adjusts by lowering the flow. Indeed when the tissues have received enough liquid such that the pressure within the tissues equals the pressure from the pump, the flow of the administered liquid will cease. In terms of patient care, this is highly advantageous because it vastly reduces the chance for accidental over medication.

As with constant pressure systems, with constant flow systems calibrated tubing and needles are once again commonly used. However, with the constant flow system, as pressure increases at the receiving site the system will increase pressure to maintain the desired flow and over medication can result. Moreover, the focus on maintaining constant pressure can result in detrimental treatment for the patient.

However, a factor in both constant flow and constant pressure is use of the correct tubing. The availability of third party tubing having a disc as taught by Sealfon '227 has introduced the possibility that despite best intentions, unwarranted tubing may be used that does not conform to the desired calibrations. As such unintended dosage may result and adversely affect the patient.

In addition, different tubing lines intended for different liquids providing different pharmaceuticals may be crossed leading to wrong substances being provided to the wrong tissues. As the use of the disc as taught by '227 is highly useful in protecting the inlet and as a brace during tubing set connection, the disc itself does not aid in avoiding misconnections.

Moreover, as the use of the disc is not in and of itself protected, although competition within the marketplace is generally good, the availability of different tubing options utilizing a disc has introduced potential problems that may adversely affect patient health and care.

Hence there is a need for a tubing set alone, and tubing set with a syringe pump which overcome one or more of the above identified challenges.

SUMMARY OF THE INVENTION

Our invention solves the problems of the prior art by providing novel systems and methods for a flared luer connector for medical tubing.

In particular, and by way of example only, according to one embodiment of the present invention, provided is a flared luer connector for medical tubing including: a tube head adapter formed of a resilient material providing: an inlet and opposite thereto an outlet with a longitudinal axis there between; a luer lock fitting formed proximate to the inlet and structured and arranged to engage a syringe; and at least one flared member disposed between the luer lock fitting and the outlet, the flared member rising from the tube head adapter and angled towards the outlet, the flared member further providing at least one engaging surface between the tube head adapter and a distal edge, the engaging surface acutely angled with respect to the longitudinal axis.

In yet another embodiment, provided is a flared luer connector for medical tubing including: a tube head adapter formed of a resilient material providing at least two members, a first member as a luer lock fitting structured and arranged to engage a syringe; and a second member as a circumferential cone axially connected adjacent to the luer lock fitting, the circumferential cone rising from the tube head adapter and flaring away from the luer lock fitting of the first member, the circumferential cone having an inner angled surface structured and arranged to engage a correspondingly angled receiver section of a base.

For yet another embodiment, provided is a syringe pump for use with a flared luer connector for medical tubing including: a housing structured and arranged to receive a syringe having a plunger movable along a barrel and an engaged tubing, the engaged tubing providing a head adapter providing a luer lock fitting engaged to the syringe and a circumferential cone rising from the head adapter and flaring away from the luer lock fitting, the circumferential cone having an inner angled surface; a base having: a longitudinal groove structured and arranged to receive at least a portion of the tubing; a receiver section extending away from the longitudinal groove and correspondingly angled to receive at least a portion of the inner angled surface of the circumferential cone; a deflector section sloping across the longitudinal groove; and an actuator structured and arranged to engage the plunger of the syringe and drive the plunger towards the tubing, the force of the actuator further engaging the inner angled surface of the circumferential cone to the receiver section of the base.

Yet for another embodiment, provided is a base for a flared luer connector for medical tubing including: a generally cylindrical body having a longitudinal groove therein structured and arranged to receive at least a portion of the flared luer connector, the cylindrical body having a first end providing: a receiver section and a deflector section with a transition zone there between; the transition zone disposed below a longitudinal centerline of the cylindrical body; the receiver section extending away from the longitudinal groove and correspondingly angled to receive at least a portion of an inner angled surface provided by the flared luer connector; and the deflector section sloping across the longitudinal groove and structured and arranged to deflect a tube head adapter having other than the flared luer connector.

For still yet another embodiment, provided is a flared luer medical tubing kit for a syringe pump including: tubing having a tube head adapter formed of a resilient material providing a luer lock fitting structured and arranged to engage a syringe, and a circumferential cone rising from the head adapter and flaring away from the luer lock fitting, the cone having an inner angled surface structured and arranged to engage a correspondingly angled receiver section of a base; a base having; a longitudinal groove structured and arranged to receive at least a portion of the tubing: a receiver section extending away from the longitudinal groove and correspondingly angled to receive at least a portion of the inner angled surface of the circumferential cone, a deflector section sloping across the longitudinal groove structured and arranged to deflect a tube head adapter having other than the circumferential cone.

And for yet another embodiment, provided is a method for using flared luer medical tubing, including: providing a tubing having a tube head adapter formed of a resilient material providing a luer lock fitting structured and arranged to engage a syringe, and a circumferential cone rising from the tube head adapter and flaring away from the luer lock fitting, the circumferential cone having an inner angled surface structured and arranged to engage a correspondingly angled receiver section of a base; engaging the luer lock fitting of the tubing to a syringe having a barrel with a plunger disposed within and movable along the barrel, the circumferential cone thus flaring away from the syringe; and disposing the syringe with engaged tubing within a pump having an actuator and a base, the base having: a longitudinal groove structured and arranged to receive at least a portion of the tubing; a receiver section extending away from the longitudinal groove and correspondingly angled to receive at least a portion of the inner angled surface of the circumferential cone; and a deflector section sloping across the longitudinal groove structured and arranged to deflect a tube head adapter having other than the circumferential cone; wherein the actuator is structured and arranged to engaged the plunger of the syringe and drive the plunger towards the tubing, the force of the actuator further engaging the inner angled surface of the circumferential cone to the receiver section of the base.

BRIEF DESCRIPTION OF THE DRAWINGS

FIGS. 3A, 3B 3C, 3D and 3E are top, bottom, front end, and perspective views of a base for use with a flared luer connector such as that shown in FIGS. 1A, 1B and 1C and 2 in accordance with at least one embodiment of the present invention;

FIG. 7 is a partial side cut through view illustrating the advantageous mating connection permitted by the flared luer connector and base in accordance with at least one embodiment of the present invention;

FIG. 8 is a partial side cut through view illustrating the advantageous rejection of a non flared luer connector when disposed to the base in accordance with at least one embodiment of the present invention;

FIGS. 10A and 10B are partial top and side exploded view of a flared luer connector, base, Syringe and Syringe Pump in accordance with at least one embodiment of the present invention;

DETAILED DESCRIPTION

Before proceeding with the detailed description, it is to be appreciated that the present teaching is by way of example only, not by limitation. The concepts herein are not limited to use or application with a specific system or method for a flared luer connector for medical tubing, a kit with flared luer medical tubing, or syringe pump for use with a flared luer connector for medical tubing. Thus although the instrumentalities described herein are for the convenience of explanation shown and described with respect to exemplary embodiments, it will be understood and appreciated that the principles herein may be applied equally in other types of systems and methods involving tubing with a flared luer.

This invention is described with respect to preferred embodiments in the following description with reference to the Figures, in which like numbers represent the same or similar elements. Further, with the respect to the numbering of the same or similar elements, it will be appreciated that the leading values identify the Figure in which the element is first identified and described, e.g., element 100 first appears in FIG. 1.

Within the medical industry small-bore connectors are commonly used to interconnect devices, tubing and accessories that deliver fluids and gasses to patients. The small connectors typically provided on tubing and which are grasped by a person for connection and disconnection are generally referred to as luer fittings, or simply luers.

The actual connection element is more properly referred to as a luer taper, of which there are two types—locking and slipping. With a luer lock the tubing and medical or laboratory equipment are twisted together as at least one luer lock fitting has threads which bind one fitting to the other. With a luer slip, the fittings are just press fit together and held by friction. Where pressure is a factor, such as with syringes, pumps or the like, the luer lock is generally favored as the threading engagement provides a tighter leak free bond.

Despite the specific origin with reference to the connection, absent a specified type of connector, when reference is made to a "luer" it is commonly understood and accepted that it is the entire end connector that is being identified. As such, as referred to herein, a flared luer is understood and appreciated to apply to the entire end fitting.

Figure 1A:
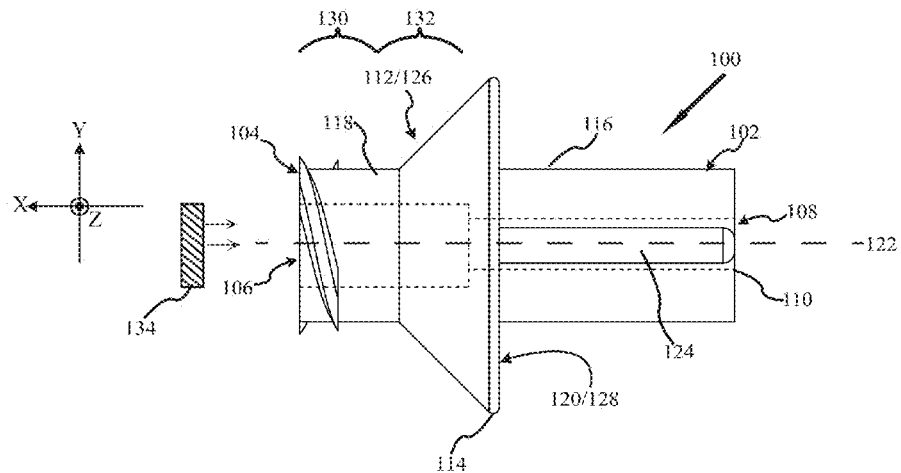
FIGS. 1A, 1B and 1C are side and perspective views of a flared luer connector in accordance with at least one embodiment of the present invention.
Figure 1B:
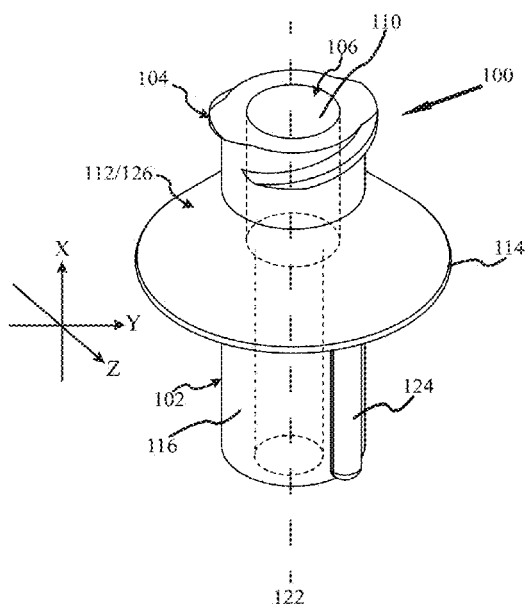
Figure 1C:
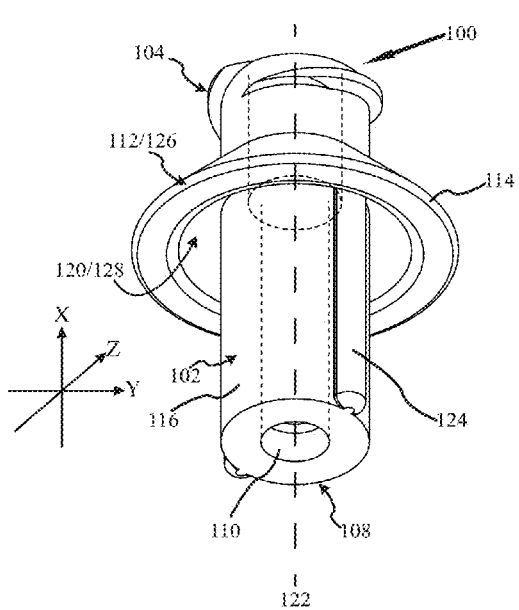

Turning now to FIG. 1, and more specifically in FIGS. 1A, 1B and 1C there is shown a flared luer connector 100 in accordance with at least one embodiment of the present invention. More specifically, for at least one embodiment the flared luer connector 100 is provided by a tube head adapter 102 formed from a resilient material such as, but not limited to polycarbonate, plastic, ceramic, or other suitable material.

To facilitate the description of systems and methods for this flared luer connector 100, the orientation of flared luer connector 100 as presented in the figures are referenced to the coordinate system with three axis orthogonal to one another as shown in FIG. 1. The axis intersect mutually at the origin of the coordinate system, which is chosen to be the center of the person's foot, however the axes shown in all figures are offset from their actual locations for clarity and ease of illustration.

As is shown, the tube head adapter 102 provides a luer lock fitting 104 proximate to an inlet 106. Tube head adapter 102 also has an outlet 108 structured and arranged to join with medical tubing. Generally the inlet 106 and the outlet 108 are provided opposite each other at either end of the flared luer connector 100 as either end of a generally straight fluid channel 110 running there through, shown conceptually by dotted lines. Of course this fluid channel 110 may change in diameter over its length between the inlet 106 and the outlet 108, be angled, or take an angled turn in some embodiments without departing from the scope of the present invention.

As shown in the accompanying illustrations, for at least one embodiment the luer lock fitting 104 has a first outer portion—shown as a thread, that is structured and arranged to fit within the cylindrical housing provided about the nozzle of a syringe. For at least one alternative embodiment, not shown, this is reversed, the luer lock fitting 104 providing an internal thread that is structured and arranged to bind directly against the nozzle of a syringe.

Disposed between the luer lock fitting 104 and the outlet 108 is at least one flared member 112 circumferentially rising from the tube head adapter 102, and angled towards the outlet 108. As used here in, the term angled as used with respect to the flared member 112 is understood and appreciated to include both flat, curved and/or other structures, which are understood and appreciated to extend other than at a general perpendicular orientation. As such, this flared member 112 has a distal edge 114 that is disposed above the tube head adapter 102 sidewall 116 and behind the point of union between the base 118 of the flared member 112 and the tube head adapter 102 sidewall 116. This flared member 112 provides at least one engaging surface 120 that is generally acutely angled with respect to the longitudinal axis 122 of the tube head adapter 102.

It should be understood and appreciated that for at least one embodiment, the distal edge 114 of the flared member 112 presents a general flat circular surface. This flat circular surface may permit the flared luer connector 100 to be used in connection with systems that are currently adapted for a disc luer.

This flared member 112 provides at least three distinct advantages:

First, as the distal edge 114 of the flared member 112 is disposed above/away from the tube head adapter 102, the flared member 112 may acct as a support to elevate the luer lock fitting 104 away from surfaces when the tube head adapter 102 is horizontally disposed upon a surface.

Second, the flared member 112 provides a foundation against which a user may brace his or her fingers when engaging or disengaging the luer lock fitting 104 to a syringe, other liquid reservoir or other device, the flared member 112 further serving to protect the luer lock fitting 104 from accidental finger contact during the engaging or disengaging process.

Third, the flared member 112 advantageously interacts with a corresponding base such as may be provided by a syringe pump, the base having a receiver section structured and arranged to receive at least a portion of the engaging surface and a deflector section structured and arranged to deflect a tube head adapter having other than the flared member 112.

For at least one embodiment, the at least one flared member 112 is more specifically described as a circumferential cone 126 rising from the tube head adapter 102 and flaring away from the luer lock fitting 104. This circumferential cone 126, and more specifically the inner surface may also be described as facing away from the luer lock fitting 104. In other words, the circumferential cone 126 expands away from the luer lock fitting 104 and the inlet 106, towards the outlet 108. To facilitate gripping by an operator, the tube head adapter 102 may also provide one or more grippers 124, such as side protrusions or a textured surface.

For at least one embodiment the circumferential cone 126 has a generally circular cross section normal to the tube head adapter 102. For yet another embodiment the circumferential cone 126 may be provided by a one or more angled surfaces. And for yet another embodiment, the circumferential cone 126 may be provided by a combination of curved and straight angled surfaces such that a cross section normal to the tube head adapter 102 has at least one straight section.

The use of a circumferential cone 126 will generally be preferred as the uniformity of the circumferential cone 126 permits use of the flared luer connector 100 without imposing a specific requirement for alignment when disposed upon the base as discussed below. Freedom from alignment is generally desirable as the luer lock fitting 104 is engaged by twisting, and a rotational alignment constraint as between the flared luer connector 100 and the base might unintentionally loosen the luer lock fitting 104 engagement.

As is further appreciated with respect to FIG. 1C, the circumferential cone 126 has an inner angled surface 128, i.e. engaging surface 120. For at least one embodiment the angle of this inner angled surface 128 is constant, which is to say that for any longitudinal cross section of the flared luer connector 100 from inlet 106 to outlet 108 the inner angled surface 128 appears as a straight line intersecting the side wall of the tube head adapter 102 proximate to the inlet 106 and rising away from the tube head adapter 102 in the general direction of the outlet 108.

For at least one alternative embodiment, the angle of this inner angled surface 128 corresponds to a parabola. As such, for any longitudinal cross section of the flared luer connector 100 from inlet 106 to outlet 108 the inner angled surface 128 appears as a curved line intersecting the side wall of the tube head adapter 102 proximate to the inlet 106 and rising away from the tube head adapter 102 in the general direction of the outlet 108.

Moreover, in varying embodiments inner angled surface 128 may comprise sections that are straight and or curved, such that the longitudinal cross section of the flared luer connector 100 from inlet 106 to outlet 108 the inner angled surface 128, appears as a straight, curved, or a combination of straight and curved line sections.

The flared member 112, such as circumferential cone 126 provides several advantages to the flared luer connector 100. For example, as is clearly evident from the associated Figures, the circumferential cone 126 extends significantly away from the tube head adapter 102. As such, when the flared luer connector 100 is disposed horizontally adjacent to a surface, the luer lock fitting 104 and the inlet 106 will more likely than not be held aloft, and thereby maintain a generally sterile state as they have not been subjected to surface contaminants. Further, the circumferential cone 126 provides a convenient brace for an operator to place the tips of his or her fingers and thumb when engaging or disengaging the luer lock fitting 104 to a syringe or other device.

And further still, the flared member 112/circumferential cone 126, and more specifically the inner angled surface 128, advantageously permits the flared luer connector 100 to impose an enhanced degree of certainty that proper tubing is used with a proper syringe pump. Use of the correct tubing can often be of paramount importance for treatments, such as infusion therapy, where the flow rate through the tubing is key for proper dosage to the patient.

Moreover, for at least one embodiment the flared luer connector 100 may be summarized as a tube head adapter 102 formed from a resilient material providing a luer lock fitting 104 structured and arranged to engage a syringe, and a circumferential cone 126 rising from the tube head adapter 102 and flaring away from the luer lock fitting 104. The circumferential cone 126 has an inner angled surface 128 structured and arranged to engage a correspondingly angled receiver section of a base.

For yet another embodiment, flared luer connector 100 may be described as having a tube head adapter 102 formed of a resilient material providing at least two members, a first member 130 as a luer lock fitting 104, structured and arranged to engage a syringe or other liquid reservoir, and a second member 132 as a flared member 112, such as circumferential cone 126 axially connected adjacent to the luer lock fitting 104 and flaring away from the luer lock fitting 104. The circumferential cone 126 has an inner angled surface 128 structured and arranged to engage a correspondingly angled receiver section of a base.

Moreover, the flared member 112 such as circumferential cone 126 is understood and appreciated to be disposed behind the luer lock fitting 104 such that the luer lock fitting 104 is free to engage a corresponding luer lock fitting provided by a syringe or other device, unencumbered.

It will also be understood and appreciated that in varying embodiments, the diameter of the luer lock fitting 104 maybe larger or smaller then the diameter of the tube head adapter 102 beneath the circumferential cone 126 and extending to the outlet 108. Indeed the use of different diameters for the luer lock fitting 104 and/or the tube head adapter 102 beneath the circumferential cone 126 and extending to the outlet 108 may advantageously permit different flared luer connectors 100 to be provided, each specifically configured for distinct uses. Based at least in part on the varying differences in size, as well as perhaps the difference in angles of the engaging surface 120, the opportunity for mismatch between a selected flared luer connector 100 and the syringe, fluid reservoir or other device to which it may be coupled is significantly reduced.

For at least one embodiment, the flared luer connector 100 may optionally be fitted with at least one filter 134 disposed within the fluid channel 110. Moreover, for at least one embodiment a filter 134 is disposed within the inlet 106. In varying embodiments, the filter 134 may be disposed further within the fluid channel 110 such that it is midway between the inlet 106 and the outlet 108.

As the flared luer connector 100 may be used in a constant pressure system, for the delivery of a liquid medication or infusion solutions to a patient, the issue of flow rate through the medical tubing to which the flared luer connector 100 is attached is of significant importance, especially when and where this tubing is flow rate control tubing—tubing that has been designed to specifically provide a given flow rate over time. The introduction of foreign materials into the tubing may restrict the flow and therefore adversely affect the intended flow rate.

Liquid medication or infusion solutions can contain particulates or foreign materials, such as glass particles from opening glass ampoules, particles generated from needles piercing rubber stoppers, and particulates present in or resulting from drug formulations. In some cases particulates are generated by freezing-thawing of drug solutions. Particulates may also result from the incomplete dissolution of drugs in solution reconstituted before infusion.

In addition to potentially causing adverse flow rates within the infusion system coupled to the flared luer connector 100, entry of particles into the body, particularly the circulatory system, by infusion can lead to potential health complications, including, among others, inflammation, sepsis, and thrombosis. As such, for at least one embodiment the flared lure connector 100 advantageously includes at least one filter 134 within the fluid channel 110.

Of course in FIGS. 1A-1C the flared luer connector 100 has been shown free of medical tubing for ease of illustration and discussion. In practice, the outlet 108 of the flared luer connector 100 is bonded, joined or otherwise fused to medical tubing such that engaging the luer lock fitting 104 to a syringe or other device will permit that syringe or other device to introduce a liquid or gas through the flared luer connector 100 and into the medical tubing.

Figure 2:
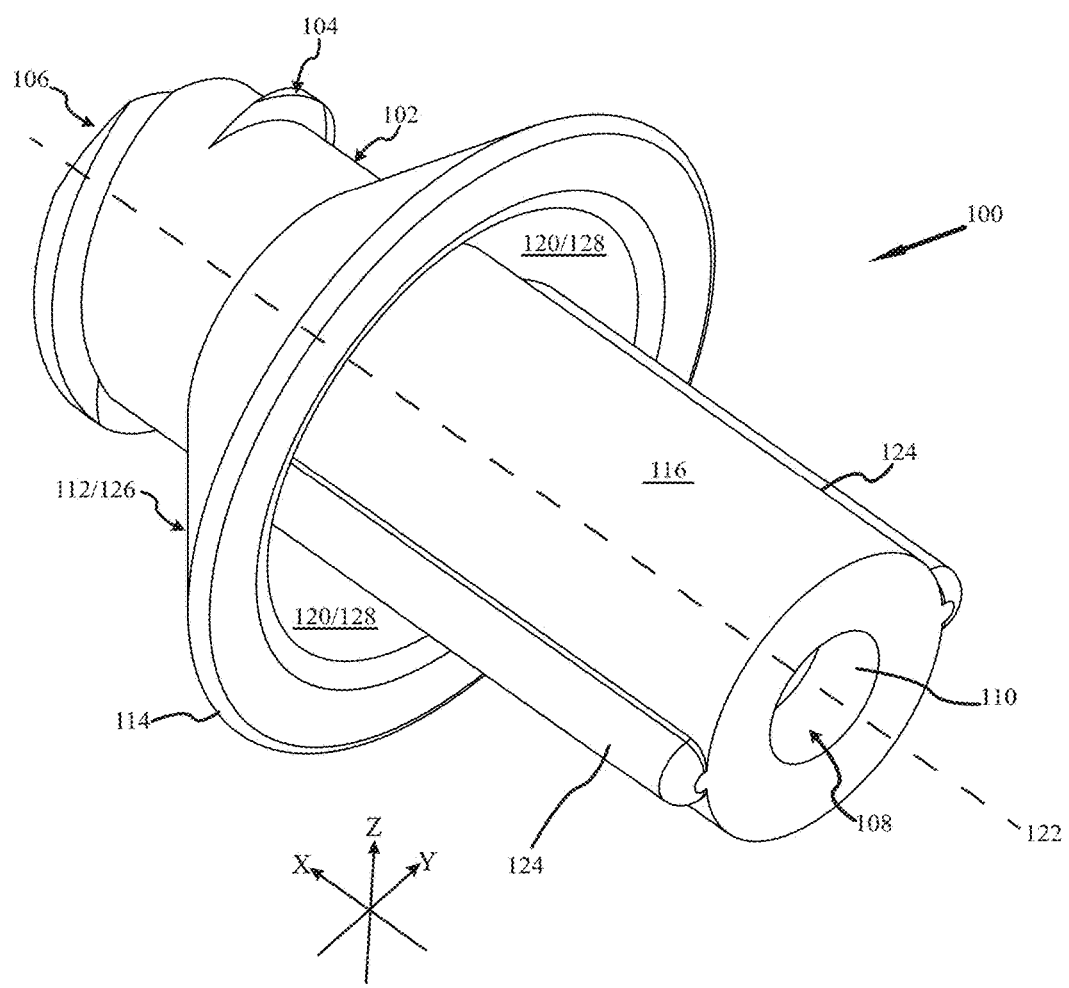
FIG. 2 is an enlarged alternative perspective view of a flared luer connector shown in FIGS. 1A-1C in accordance with at least one embodiment of the present invention.

FIG. 2 provides an enlarged perspective view of flared luer connector 100 further illustrating the relative size and placement of the circumferential cone 126, grippers 124 and luer lock fitting 104 as provided about the tube head adapter 102.

As noted above, at least one advantageous aspect of the flared luer connector 100 is the enhanced ability to ensure the use of the proper tubing attached to the flared luer connector 100 with respect to an intended syringe, reservoir or other device. This advantageous ability is further achieved through the use of a corresponding base having a receiver section structured and arranged to mate with the engaging surface 120 of the flared luer connector 100.

With respect to the above description and exemplary description of the flared luer connector 100, it will be understood and appreciated that the flared luer connector 100 may be fabricated in a number of different ways. For example, and not by limitation, in at least one embodiment the flared luer connector 100 may be injection molded, milled or otherwise formed, as a single piece. The fluid channel 110 may be cast/molded/formed as well, or later drilled.

Alternatively, the tube head adapter 102 and the flared member 112, i.e., the circumferential cone 126 may be separately cast, molded or otherwise formed and then assembled together, such as by snap fitting, gluing or otherwise bonding the circumferential cone 126 about the tube head adapter 112. Indeed, the circumferential cone 126 may include two cutouts to accommodate passage of the grippers 124 through the circumferential cone 126 during assembly, such cutouts not otherwise altering or otherwise affecting the performance of the circumferential cone 126 as is further described herein.

The following FIGS. 3A, 3B, 3C, 3D, 4A and 4B will now be discussed with respect to this advantageous base 300. Moreover, it should be understood and appreciated that although the flared luer connector 100 and base 300 are distinct physical components which may be manufactured, packaged and distributed separately, they are intended to cooperatively interact with one another.

In FIGS. 3A, 3B, 3C, 3D and 3E there is shown a base 300 in accordance with at least one embodiment of the present invention, FIG. 3A being a top view, FIG. 3B being a bottom view, FIG. 3C being a front view, FIG. 3D being a side perspective view from the first end and FIG. 3E being a side perspective view from the second end. More specifically, the base 300 is provided by a generally cylindrical body 302 having a longitudinal groove 304 therein structured and arranged to receive at least a portion of the tube head adapter 102. Further, the base 300 has a first end 306 which provides a receiver section 308 and a deflector section 310, with a transition zone 312 there between. The longitudinal groove 304 is generally disposed about longitudinal centerline 314.

Figure 4A:
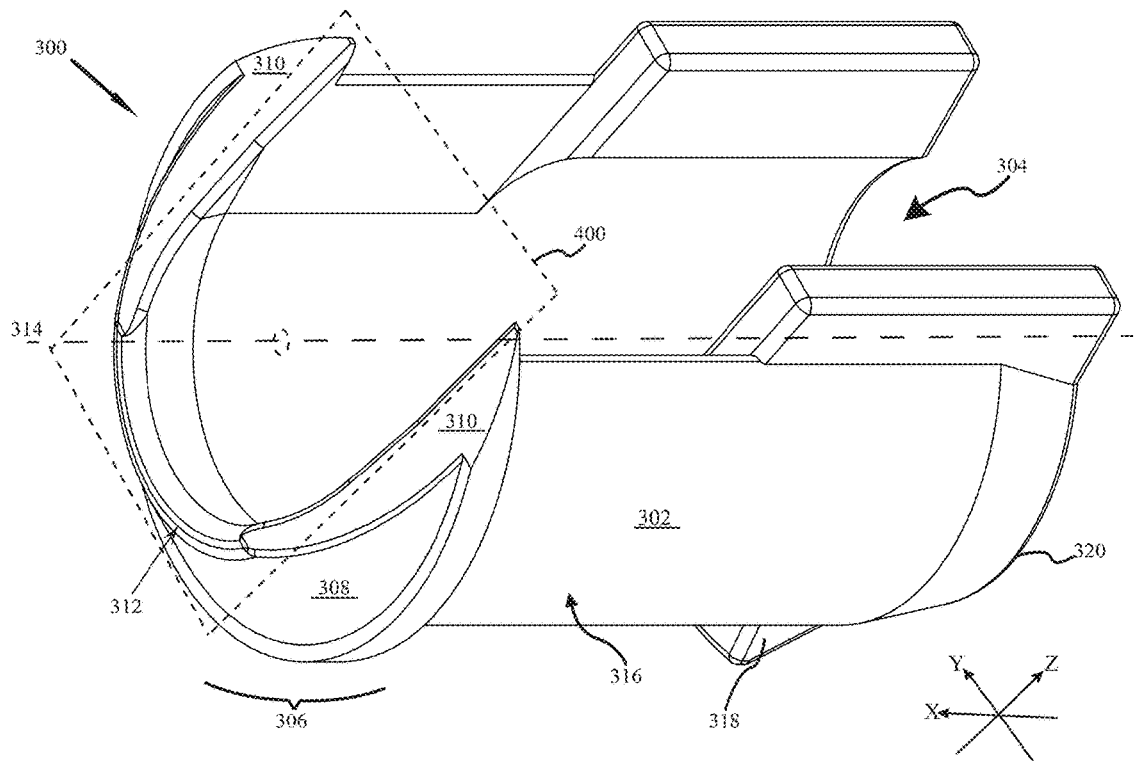
FIGS. 4A and 4B are an enlarged alternative perspective view and side view of a base as shown in FIGS. 3A-3C in accordance with at least one embodiment of the present invention.
Figure 4B:
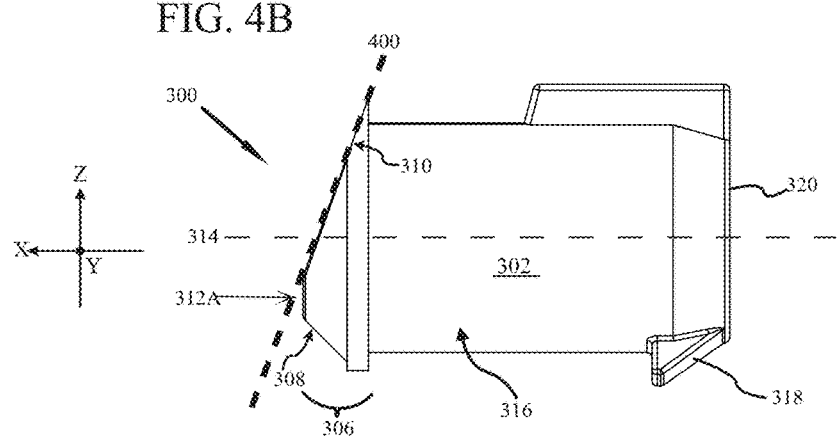

As may be further appreciated in the figures, the transition zone 312 is offset from the longitudinal centerline 314, and with respect to FIG. 4B showing the side view of base 300, for at least one embodiment the forward most part of the transition zone 312A is disposed below the longitudinal centerline 314.

Moreover, for at least one embodiment the base 300 may be summarized as a generally cylindrical body 302 having a longitudinal groove 304 therein structured and arranged to receive at least a portion of the flared luer connector 100, the cylindrical body 302 having a first end 306 providing: a receiver section 308 and a deflector section 310 with a transition zone 312 there between. The transition zone 312 is disposed below a longitudinal centerline 314 of the cylindrical body 302. The receiver section 308 extends away from the longitudinal groove 304 and correspondingly angled to receive at least a portion of an inner angled surface 128/engaging surface 120, provided by the flared luer connector 100. The deflector section 310 sloping across the longitudinal groove 304 and structured and arranged to deflect a tube head adapter other than the flared luer connector 100.

For at least one embodiment, the base 300 may also be provided as an insert 316 with at least one attacher 318 such that it may be disposed in an existing syringe pump or other base housing so as to permit operation of the syringe pump or other device in connection with the flared luer connector 100. For yet an alternative embodiment, the base 300 may be provided as an incorporated element of a syringe pump or other device to permit operation with the flared luer connector 100.

For the exemplary embodiment as shown, the attacher 318 has been shown as a friction locking tooth disposed proximate to the second end 320 of the cylindrical body 302. In varying embodiments, the attacher 318 may be one or more pins, teeth, flanges or other appropriate mechanical device(s) that extend from the midsection or second end 320 of the cylindrical body 302 and which are capable of at least temporarily binding the insert 316 to a base housing.

As is perhaps more clearly shown in FIGS. 4A and 4B showing an enlarged perspective and side view of the base 300, the receiver section 308 is provided below the longitudinal centerline 314 of the cylindrical body 302. Further still, the receiver section 306 is a curved section rising away from the longitudinal centerline 314 and flaring towards the second end 320 of the base 300.

In contrast to the receiver section 308, the deflector section 310 generally defines a plane 400 sloping across the longitudinal centerline 314 and at least a portion of the longitudinal groove 304. Moreover, the transition zone 312 between the receiver section 308 and the deflector section 310 is radially offset from the longitudinal centerline 314 and longitudinal groove 304.

This radial offset of the transition zone 312 advantageously ensures that the base 300 can receive a corresponding flared luer connector 100, but will otherwise reject, and actually eject, a traditional luer connector or improperly selected flared luer connector 100. This functional ability to accept or reject a luer connector is based at least in part on the relative alignment of the receiver section 308 and the deflector section 310 in relation to the longitudinal centerline 314 of the base 300 as well as the inner angled surface 128 of the circumferential cone 126. These elements and this relationship is further illustrated in FIGS. 5 and 6.

Figure 5A:
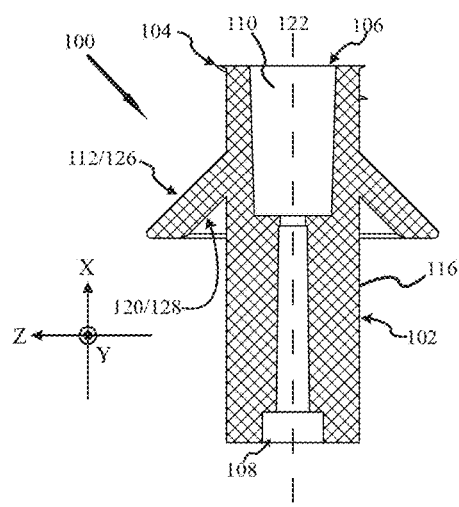
FIGS. 5A and 5B are side and corresponding cut through views of a flared luer connector in accordance with at least one embodiment of the present invention.
Figure 5B:
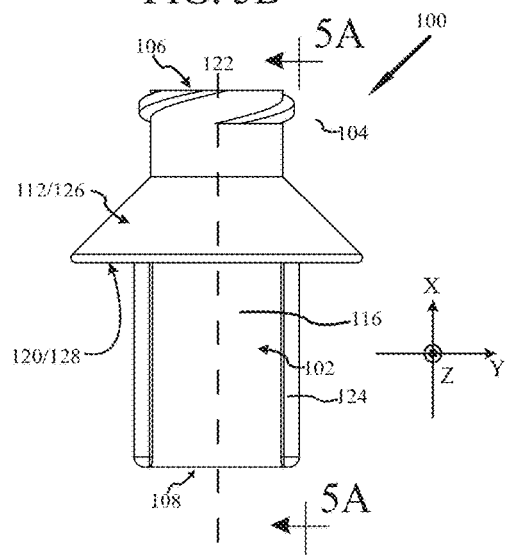
Figure 6A:
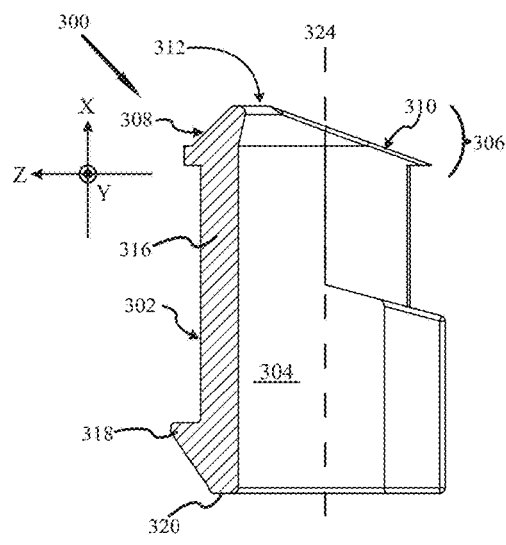
FIGS. 6A and 6B are side and corresponding cut through views of a base in accordance with at least one embodiment of the present invention.
Figure 6B:
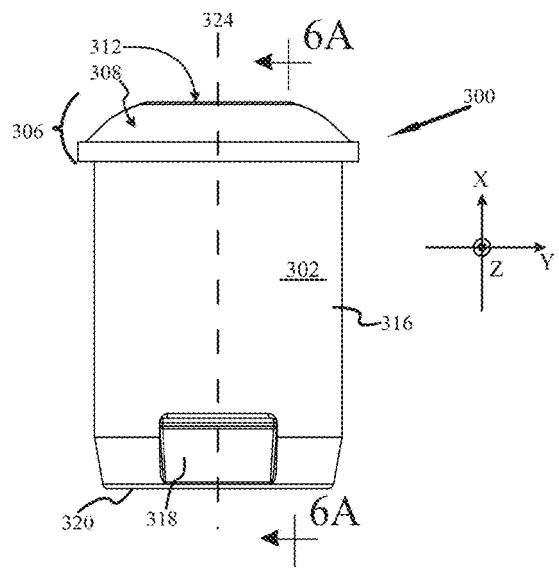

More specifically, FIGS. 5A and 5B present a side view and cut through view along the longitudinal axis 122 of the flared luer connector 100. Likewise, FIGS. 6A and 6B present a bottom side and cut through view along the long the longitudinal centerline 314 of the base 300. As is clearly shown in FIG. 6A, the transition zone 312 between the receiver section 308 and the deflector section 310 is displaced away from the longitudinal centerline 314 of the base 300.

As such, the transition zone 312 will fall within the circumferential cone 126 when the flared luer connector 100 is disposed within the longitudinal groove 304 of the base 300. More significantly, the receiver section 308 will align with at least a portion of the inner angled surface 128 of the circumferential cone 126 so as to receive and support at least a portion of the circumferential cone 126. Moreover, the corresponding angles of the inner angled surface 128 and the receiver section 308 advantageously permit the flared luer connector 100 to be snuggly disposed upon and retained by the base 300.

FIG. 7 conceptually illustrates this. As shown, in Step I, the flared luer connector 100 is moved towards base 300 as shown by lateral force arrows 700. In Step II, the flared member 112/circumferential cone 126, of flared luer connector 100 is about to engage with the base 300, and more specifically the receiver section 308 of the base. In Step III, the engaging surface 120 of the flared member 112/circumferential cone 126 has indeed engaged with the receiver section 308, and the flared luer connector 100 is secure.

In advantageous contrast to the mating that will occur between the base 300 and a corresponding flared luer connector 100, should a tube head adapter having a flat disc be disposed against the base 300 with at least a portion of the tube head adapter disposed within the longitudinal groove 304, when pressure is applied to the tube head adapter axially along the longitudinal axis, the disc will meet the transition zone 312 and a rotational torque force will develop driving the disc up and along the deflector section 310 such that the improper tube head will be expelled from the base 300.

FIG. 8 conceptually illustrates this. As shown in Step I, a disc luer connector 800 is moved towards base 300 as shown by lateral force arrows 802. In Step II, the disc 804 of the disc luer connector 800 is about to engage with the base 300. The disc 804 does not provide an engaging surface for the receiver section 308. In Step III, as such, as lateral force 802 is continually applied, the disc 804 makes contact with the transition zone 312 and the disc luer connector 800 tilts and is driven up and away from the transition zone 312. As shown in Step IV, the disc luer connector 800 is ejected from the base 300.

Moreover, a tube head adapter which does not have a properly corresponding flared member 112, shown as exemplary circumferential cone 126, will be expelled. As such, operators and or users of medical tubing equipped with the flared luer connector 100 are assured that only properly mating medical tubing coupled to a syringe may be disposed in a syringe pump configured with a corresponding base 300.

Figure 9:
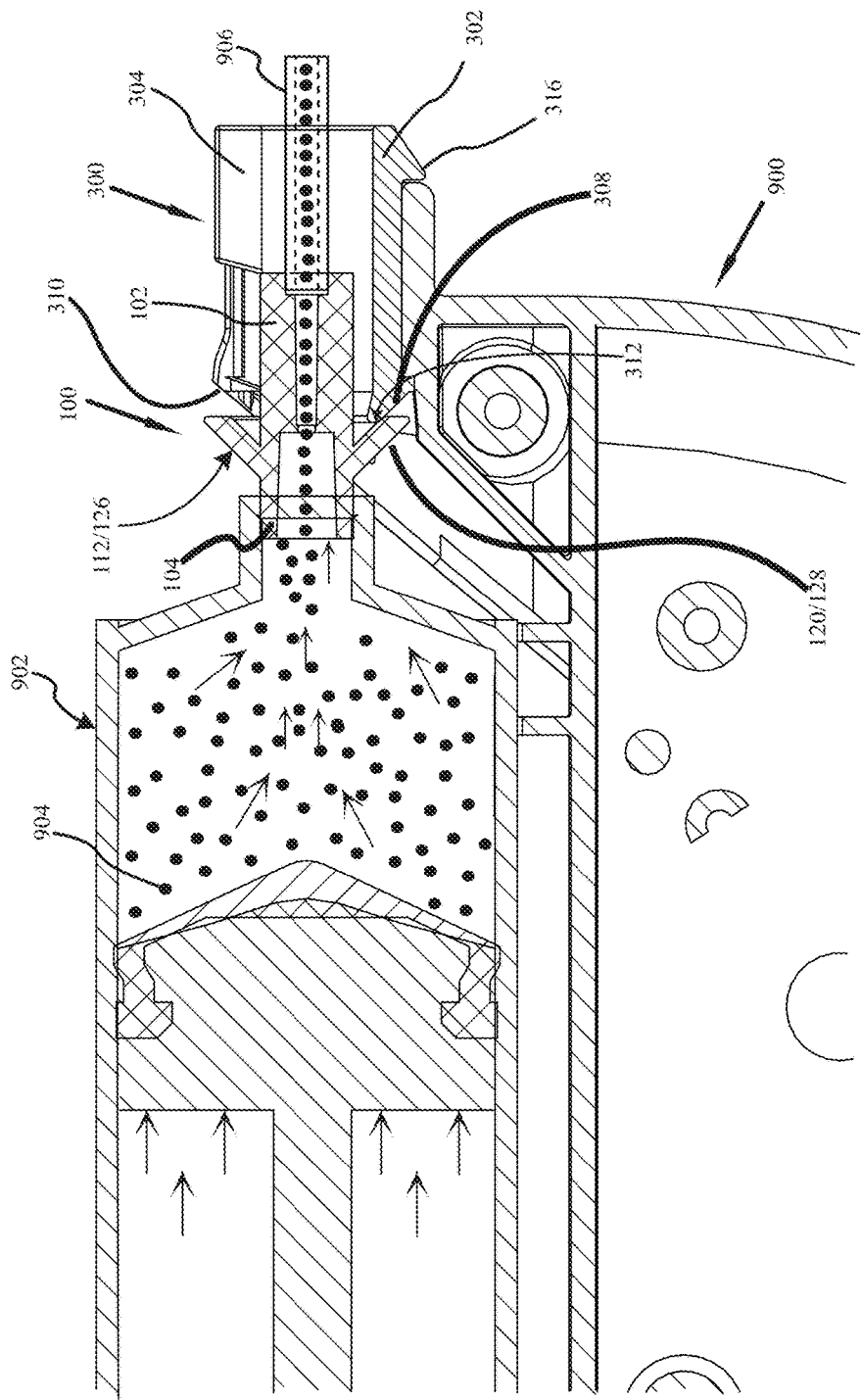
FIG. 9 is a partial side cut through view of a flared luer connector coupled to a Syringe and disposed in a Syringe Pump having a base receiving the Flared Luer Connector in accordance with at least one embodiment of the present invention.

FIG. 9 presents a partial enlarged cross section of a syringe pump system 900 configured with a base 300 that has received a syringe 902 coupled by the luer lock fitting 104 to a flared luer connector 100. In this cross sectional view, the mating alignment of the receiver section 308 and the inner angled surface 128 of the circumferential cone 126 may be further appreciated.

With respect to this cut away view, it is also to be appreciated that for at least one embodiment, the receiver section 308 contacts only a portion of the inner angled surface 128 and does not extend all the way forward to the inner base of the circumferential cone 126 where it is joined to the tube head adapter 102.

In other words, the transition zone 312 between the receiver section 308 and the deflector section 310 is adjacent to a mid area of the inner angled surface 128 and therefore offset from the tube head adapter 102. As shown in the exemplary illustrations of FIG. 8, for at least one embodiment this offset of the transition zone 312 increases the effectiveness of the deflector section 306 to aid in the ejection of a tube head adapter 102 providing other than a corresponding circumferential cone 126.

When properly engaged as shown, the flared luer connector 100 binds against the base 300 as pressure is applied by the syringe pump system 900. Fluid, conceptualized by dots 904, from within the syringe 902 is directed into the flared luer connector 100 and consequently into the medical tubing 906 bonded thereto, and thus can be delivered to a patient in accordance with his or her specified treatment, such as for example, an infusion therapy treatment.

In addition, the safety of using the flared luer connector 100, base 300 and syringe pump 900 is also enhanced. As is more fully appreciated with respect to the accompanying figures as described, the receiver section 308 will tip down the syringe with a proper flared luer connector 100. Thus, even if the patient has not placed the syringe in the syringe pump 900 correctly, in some cases rather than being ejected, as the plunger is driven forwards, the flared member 112/circumferential cone 126 will engage with the receiver section 308 of the base 300 and guide the syringe 902 into a proper and snug fitting such that all components are properly aligned and in their designated areas.

The use of the base 300 as an insert 316 permits use of the base 300 and flared luer connector 100 with existing syringe pump systems 900 that currently provide a different base for receiving legacy tube head adapters. Of course, as noted above for at least one embodiment, the base 300 is provided as an integral component of the syringe pump system 900.

FIGS. 10A and 10B present a partial top and side exploded view of the flared luer connector 100, base 300, syringe 902, and syringe pump system 900 further illustrating the general alignment of the various components, i.e., the flared luer connector 100, base 300, syringe 902, and syringe pump system 900. For the particular exemplary embodiment shown, the syringe pump 900 is a Freedom60® Syringe Infusion System as provided by RMS Medical Products of Chester, N.Y.

Figure 11:
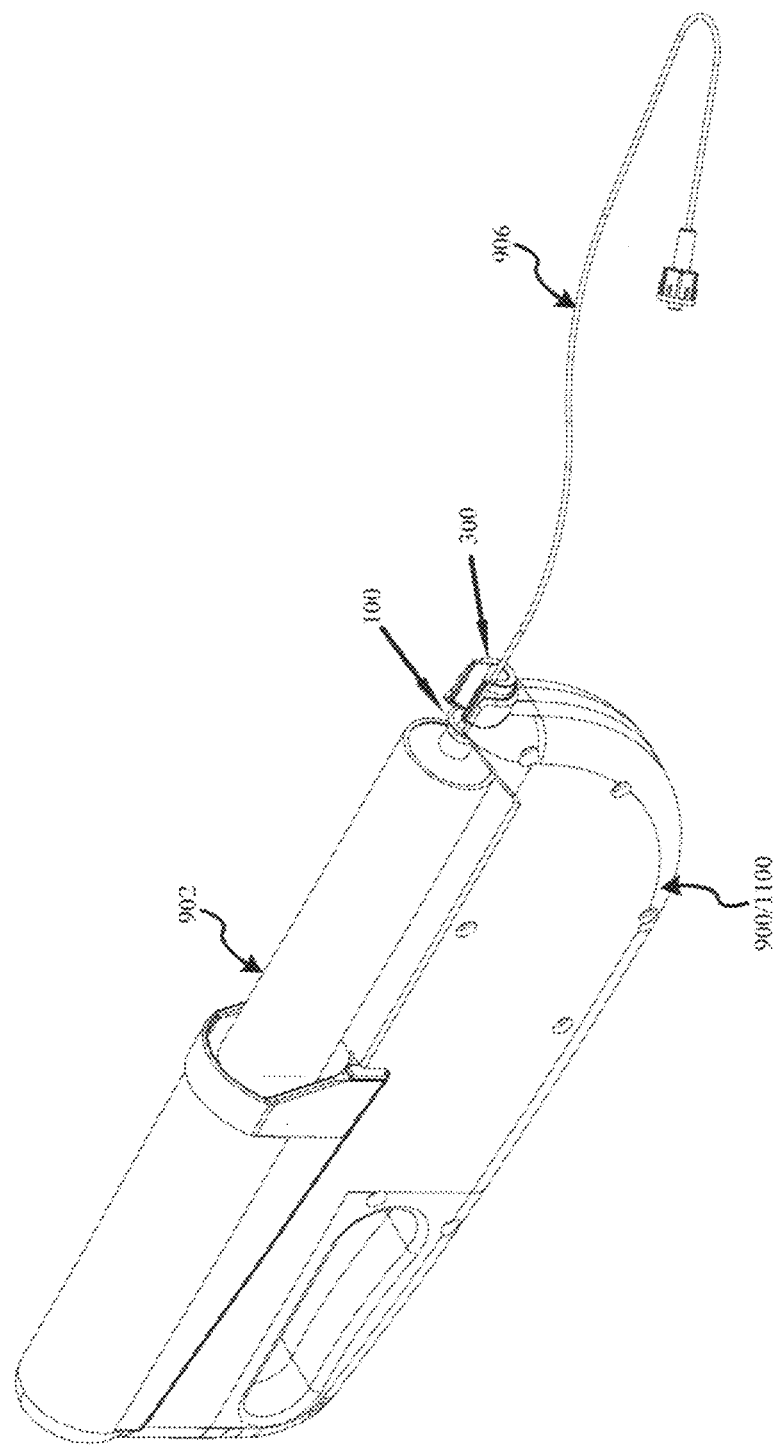
FIG. 11 is a side perspective view of the flared luer connector, base, syringe and syringe pump system in an assembled and ready to use state in accordance with at least one embodiment of the present invention.

FIG. 11 is a perspective view of the flared luer connector 100, base 300, syringe 902, and syringe pump system 900 in an assembled state with medical tubing 904, the assembled system thus being ready for use. Again, as in FIGS. 10A and 10B the exemplary embodiment shown utilizes the flared luer connector 100 and base 300 in connection with syringe pump 900 being a Freedom60® Syringe Infusion System 1100 as provided by RMS Medical Products of Chester, N.Y.

It should be understood and appreciated that different embodiments of base 300 may be provided for different types of syringe pumps. This may advantageously further permit specific and dedicated use of a specific base 300 with a specific type of syringe pump. FIGS. 12A-12E further illustrate such an embodiment, where base 300 is provided as base 1200 for use specifically with the FreedomEdge Syringe Infusion System as provided by RMS Medical Products of Chester, N.Y.

Figure 12A:
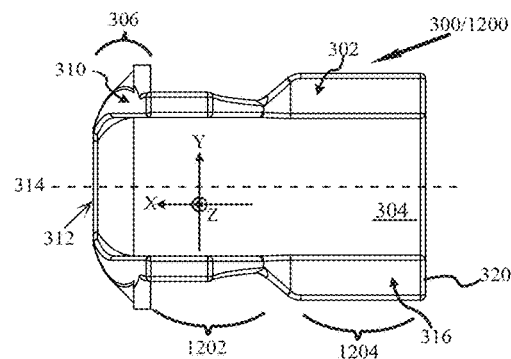
FIGS. 12A, 12B 12C, 12D and 12E are top, bottom, front end, and perspective views of an alternative base for use with a flared luer connector such as that shown in FIGS. 1A, 1B and 1C and 2 in accordance with at least one embodiment of the present invention.
Figure 12B:
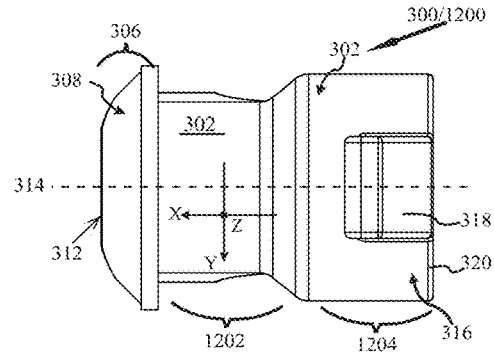
Figure 12C:
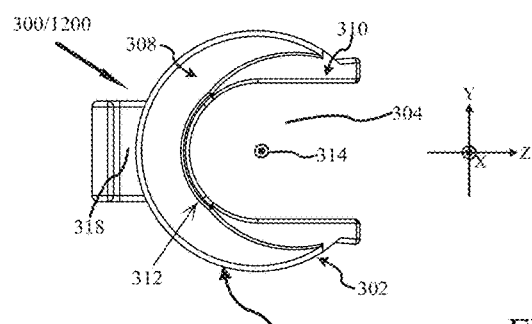
Figure 12D:
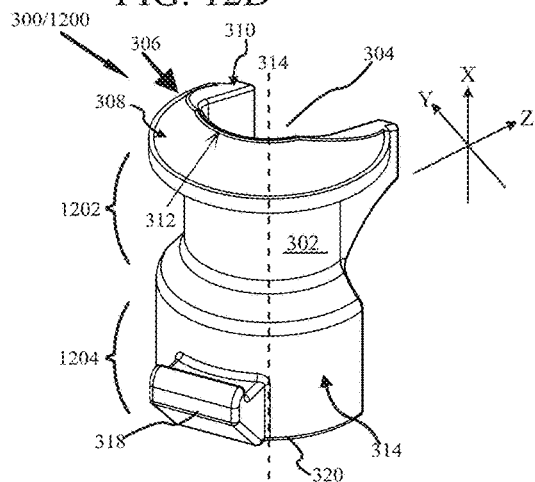
Figure 12E:
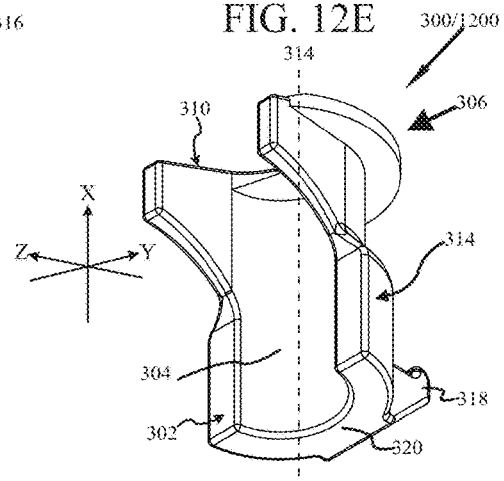

As shown, FIG. 12A is a top view, FIG. 12B is a bottom view, FIG. 12C is a front view, FIG. 12D is a side perspective view from the first end and FIG. 12E is a side perspective view from the second end. Indeed FIGS. 12A-12E generally parallel FIGS. 3A-3E. Specifically, the base 300/1200 is provided by a generally cylindrical body 302 having a longitudinal groove 304 therein structured and arranged to receive at least a portion of the tube head adapter 102.

Further, the base 300 has a first end 306 which provides a receiver section 308 and a deflector section 310, with a transition zone 312 there between. The longitudinal groove 304 is generally disposed about longitudinal centerline 314.

Moreover, for at least one embodiment the base 300/1200 may be summarized as a generally cylindrical body 302 having a longitudinal groove 304 therein structured and arranged to receive at least a portion of the flared luer connector 100, the cylindrical body 302 having a first end 306 providing: a receiver section 308 and a deflector section 310 with a transition zone 312 there between. The transition zone 312 is disposed below a longitudinal centerline 314 of the cylindrical body 302. The receiver section 308 extends away from the longitudinal groove 304 and is correspondingly angled to receive at least a portion of an inner angled surface 128 provided by the flared luer connector 100. The deflector section 310 slopes across longitudinal groove 304 and is structured and arranged to deflect a tube head adapter other than the flared luer connector 100.

Indeed the advantageous distinction between embodiments for a base 300 adaptable for the Freedom60® Syringe Infusion System and a base 1200 adaptable for the the FreedomEdge Syringe Infusion System is achieved by cylindrical body 302 for the Freedom60® having a generally consistent geometry, whereas the cylindrical body 302 for the FreedomEdge has a changing geometry, with at least two different zones, i.e. first zone 1202 and second zone 1204. For both, in at least one embodiment for each, the longitudinal groove 304 is substantially identical, such that either base 300 or base 1200 may receive the same flared luer connector 100.

Figure 13:
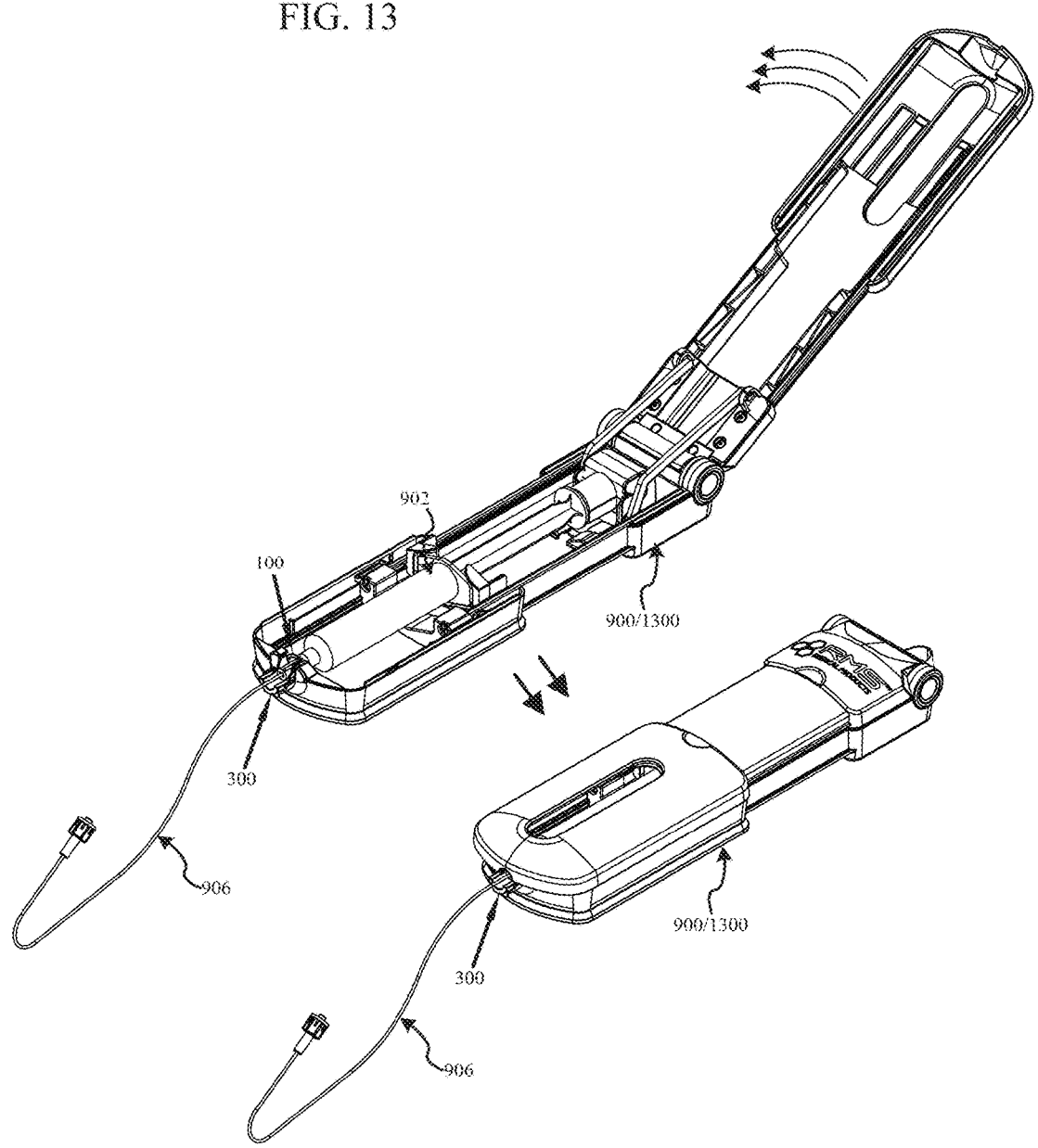
FIG. 13 is a side perspective view of the flared luer connector, base, syringe and syringe pump system in an alternative assembled and ready to use state in accordance with at least one embodiment of the present invention.

FIG. 13 is a perspective view of the flared luer connector 100, base 300, syringe 902, and syringe pump system 900 in an assembled state with medical tubing 904, the assembled system thus being ready for use. For this exemplary embodiment as shown the flared luer connector 100 and base 300 in connection with syringe pump 900 being a FreedomEdge Syringe Infusion System 1300 as provided by RMS Medical Products of Chester, N.Y. The FreedomEdge 1300 is shown open, and again with the top cover closed as when in actual use.

With respect to the above description of the flared luer connector 100 and base 300, for at least one embodiment the base 300 and tubing 906 having a flared luer connector 100 may be provided as a kit, the kit prepared and provided in a sterile packaging for use when and as desired.

Having described embodiments of the flared luer connector 100, other embodiments relating to at least one method of using a flared luer connector 100 will now be discussed. It will be appreciated that the described method need not be performed in the order in which it is herein described, but that this is merely exemplary of one method of using a flared luer connector 100.

Figure 14:
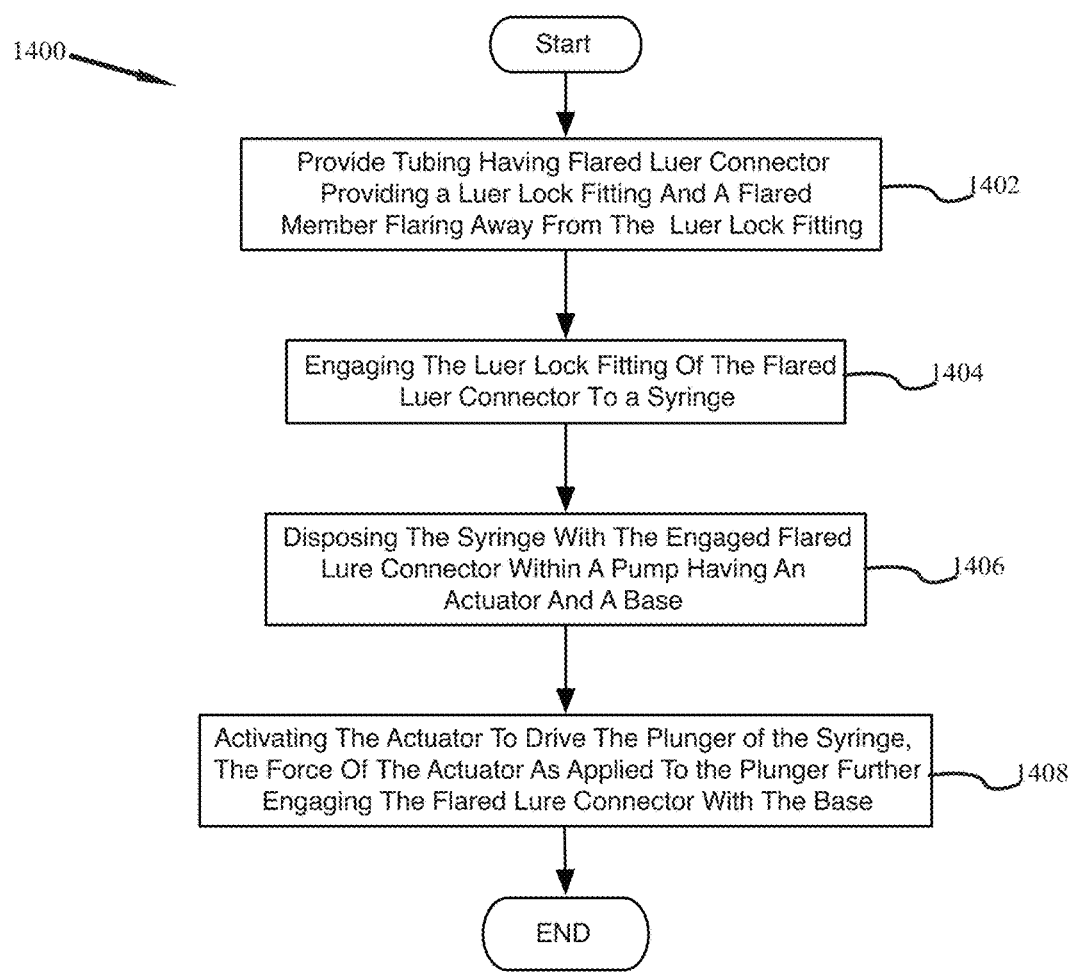
FIG. 14 is a high level flow diagram conceptualizing a method of using a flared luer connector and base in accordance with at least one embodiment of the present invention.

Turning now to FIG. 14, in general, for at least one embodiment the method 1400 commences with providing tubing 906 having a flared luer connector 100 with a luer lock fitting 104 and a flared member 112, such as a circumferential cone 128, block 1402. More specifically, as described above, for at least one embodiment the flared luer connector 100 is provided by a tube head adapter 102 formed of a resilient material providing a luer lock connector 104 structured and arranged to engage a syringe 902.

As described above, for at least one embodiment, the tube head adapter 102 has a circumferential cone 126 rising from the tube head adapter 102 and flaring away from the luer lock fitting 104. As noted above, the circumferential cone 126 has an inner angled surface structured and arranged as an engaging surface 120 to engage a correspondingly angled receiver section 308 of a base 300.

The method continues with engaging the luer lock fitting 104 of the flared luer connector 100 to a syringe 902 having a barrel with a plunger disposed within and movable along the barrel, the circumferential cone 126 thus flaring away from the syringe 902, block 1204. Next, the syringe 902 with engaged flared luer connector 100 and tubing 906 is disposed within a syringe pump system 900 an actuator and a base 300, block 1406.

As described above, the base 300 has a longitudinal groove 304 structured and arranged to receive at least a portion of the tube head adapter 102. The base 300 further has a receiver section 308 extending away from the longitudinal groove 304 and correspondingly angled to receive at least a portion of the inner angled surface 128 of the circumferential cone 126, i.e. the engaging surface 120. The base 300 also has a deflector section 310 sloping across the longitudinal groove 304, the deflector section 310 structured and arranged to deflect a tube head adapter having other than the flared luer connector 100.

The method continues with activating the actuator of the syringe pump, block 1408, which when activated is structured and arranged to engage the plunger of the syringe and drive the plunger towards the flared luer connector 100 and tubing 906. The force of the actuator further engaging the inner angled surface 128 of the circumferential cone 126 to the receiver section 308 of the base 300.

Changes may be made in the above methods, systems and structures without departing from the scope hereof. It should thus be noted that the matter contained in the above description and/or shown in the accompanying drawings should be interpreted as illustrative and not in a limiting sense. Indeed many other embodiments are feasible and possible, as will be evident to one of ordinary skill in the art. The claims that follow are not limited by or to the embodiments discussed herein, but are limited solely by their terms and the Doctrine of Equivalents.

What is claimed:

1. A flared luer connector for medical tubing comprising:
  a tube head adapter formed of a resilient material providing:
    an inlet and opposite thereto an outlet with a longitudinal axis there between;
    a luer lock fitting formed proximate to the inlet and structured and arranged to engage a syringe; and
    at least one flared member disposed between the luer lock fitting and the outlet, the flared member rising from the tube head adapter and angled towards the outlet, the flared member further providing at least one inner engaging surface between the tube head adapter and a distal edge, the inner engaging surface acutely angled toward the outlet with respect to the longitudinal axis.

2. The flared luer connector of claim 1, wherein the engaging surface is structured and arranged to engage a correspondingly angled receiver section of a base, the base having an angled deflector section structured and arranged to deflect a tube head adapter having other than the flared member.

3. The flared luer connector of claim 2, wherein the base is an insert provided to a syringe pump.

4. The flared luer connector of claim 2, wherein the base is a component of a syringe pump.

5. The flared luer connector of claim 1, wherein the tube head adapter further provides at least one gripper structured and arranged for gripping by an operator as the luer lock fitting is engaged with a syringe.

6. The flared luer connector of claim 1, wherein the angle of the acutely angled inner engaging surface is constant.

7. The flared luer connector of claim 1, wherein the angle of the acutely angled inner engaging surface corresponds to a parabola.

8. The flared luer connector of claim 1, wherein the flared member elevates the luer lock fitting away from a surface when the tube head adapter is disconnected from the syringe and at least partially disposed horizontally upon a surface.

9. The flared luer connector of claim 1, wherein the tube head adapter is generally cylindrical.

10. The flared luer connector of claim 1, wherein the luer lock fitting has a first outer portion structured and arranged to fit within a cylindrical housing, the flared member disposed about the tube head adapter behind the first outer portion.

11. The flared luer connector of claim 1, wherein the flared member is a circumferential cone rising from the tube head adapter and flaring away from the luer lock fitting.

12. The flared luer connector of claim 11, wherein the circumferential cone has a generally circular cross section normal to the tube head adapter.

13. The flared luer connector of claim 11, wherein the circumferential cone is provided by a plurality of sections such that a cross section normal to the tube head adapter has at least one straight section.

14. The flared luer connector of claim 1, wherein the flared luer connector is joined to medical tubing.

15. The flared luer connector of claim 1, further including at least one filter disposed in a fluid channel between the inlet and the outlet.

16. A flared luer connector for medical tubing comprising:
a tube head adapter formed of a resilient material providing at least two members, a first member as a luer lock fitting structured and arranged to engage a syringe; and
a second member as a circumferential cone axially connected adjacent to the luer lock fitting, the circumferential cone rising from the tube head adapter and flaring away from the luer lock fitting of the first member, the circumferential cone having an inner angled surface oriented away from the luer lock fitting, at least a portion of the inner angled surface structured and arranged to engage a correspondingly angled receiver section of a base.

17. The flared luer connector of claim 16, wherein the second member is axially connected behind the luer lock fitting of the first member.

18. The flared luer connector of claim 16, wherein the tube head adapter further provides at least one gripper structured and arranged for gripping by an operator as the luer lock fitting is engaged with a syringe.

19. The flared luer connector of claim 16, wherein the tube head adapter is generally cylindrical.

20. The flared luer connector of claim 16, wherein the circumferential cone elevates the luer lock fitting away from a surface when the tube head adapter is disconnected from the syringe and at least partially disposed horizontally upon a surface.

21. The flared luer connector of claim 16, wherein the circumferential cone has a generally circular cross section normal to the tube head adapter.

22. The flared luer connector of claim 16, wherein the angle of the inner angled surface is constant.

23. The flared luer connector of claim 16, wherein the angle of the inner angled surface corresponds to a parabola.

24. The flared luer connector of claim 16, wherein the circumferential cone is provided by a plurality of sections such that a cross section normal to the head adapter has at least one straight section.

25. The flared luer connector of claim 16, wherein the flared luer connector is joined to medical tubing.

26. The flared luer connector of claim 16, wherein the tube head adapter provides an inlet adjacent to the luer lock fitting and opposite thereto an outlet with a fluid channel there between, the flared luer connector further including at least one filter disposed within the fluid channel.

27. A syringe pump for use with a flared luer connector for medical tubing comprising:
a housing structured and arranged to receive a syringe having a plunger movable along a barrel and an engaged tubing, the engaged tubing providing a head adapter providing a luer lock fitting engaged to the syringe and a circumferential cone rising from the head adapter and flaring away from the luer lock fitting, the circumferential cone having an inner angled surface;
a base having:
a generally cylindrical body having a longitudinal groove therein structured and arranged to receive at least a portion of the flared luer connector, the cylindrical body having a first end providing;
a receiver section and a deflector section with a transition zone there between;
the transition zone disposed below a longitudinal centerline of the cylindrical body
the receiver section extending away from the longitudinal groove and correspondingly angled to receive at least a portion of an inner angled surface provided by the flared luer connector; and
the deflector section sloping across the longitudinal groove; and
an actuator structured and arranged to engage the plunger of the syringe and drive the plunger towards the engaged tubing, a force of the actuator further engaging the inner angled surface of the circumferential cone to the receiver section of the base.

28. The syringe pump of claim 27, wherein the deflector section is structured and arranged to deflect a tube head adapter having other than the circumferential cone.

29. The syringe pump of claim 27, wherein a transition zone between the receiver section and the deflector section is radially offset from the longitudinal groove.

30. The syringe pump of claim 27, wherein the base is a component of a syringe pump.

31. The syringe pump of claim 27, wherein the base is an insert structured and arranged to couple with a base housing.

32. The syringe pump of claim 27, wherein the receiver section has a generally circular cross section normal to the longitudinal groove.

33. The syringe pump of claim 27, wherein the angle of the receiver section is constant.

34. The syringe pump of claim 27, wherein the angle of the receiver section corresponds to a parabola.

35. A base for a flared luer connector for medical tubing comprising:
a generally cylindrical body having a longitudinal groove therein structured and arranged to receive at least a portion of the flared luer connector, the cylindrical body having a first end providing:
a receiver section and a deflector section with a transition zone there between;
the transition zone disposed below a longitudinal centerline of the cylindrical body;

the receiver section extending away from the longitudinal groove and correspondingly angled to receive at least a portion of an inner angled surface provided by the flared luer connector; and the deflector section sloping across the longitudinal groove and structured and arranged to deflect a tube head adapter other than the flared luer connector.

36. The base of claim 35, wherein a transition zone between the receiver section and the deflector section is radially offset from the longitudinal groove.

37. The base of claim 35, wherein the base is a component of a syringe pump.

38. The base of claim 35, wherein the base is an insert structured and arranged to couple with a base housing.

39. The base of claim 38, wherein the base housing is a FreedomeEdge Syringe Infusion System.

40. The base of claim 38, wherein the base housing is a Freedome60® Syringe Infusion System.

41. The base of claim 35, wherein the receiver section has a generally circular cross section normal to the longitudinal groove.

42. The base of claim 35, wherein the angle of the receiver section is constant.

43. The base of claim 35, wherein the angle of the receiver section corresponds to a parabola.

44. The base of claim 35, wherein the flared luer connector includes:

a tube head adapter formed of a resilient material providing:
an inlet and opposite thereto an outlet with a longitudinal axis there between;
a luer lock fitting formed proximate to the inlet and structured and arranged to engage a syringe; and
at least one flared member disposed between the luer lock fitting and the outlet, the flared member rising from the tube head adapter and angled towards the outlet, the flared member further providing at least one inner angled surface between the tube head adapter and a distal edge, the inner angled surface acutely angled toward the outlet with respect to the longitudinal axis.

45. A flared luer medical tubing kit for a syringe pump comprising:

tubing having a tube head adapter formed of a resilient material providing a luer lock fitting structured and arranged to engage a syringe, and a circumferential cone rising from the tube head adapter and flaring away from the luer lock fitting, the cone having an inner angled surface structured and arranged to engage a correspondingly angled receiver section of a base;

a base having:
a generally cylindrical body having a longitudinal groove therein structured and arranged to receive at least a portion of the flared luer connector, the cylindrical body having a first end providing;
a receiver section and a deflector section with a transition zone there between;
the transition zone disposed below a longitudinal centerline of the cylindrical body;
the receiver section extending away from the longitudinal groove and correspondingly angled to receive at least a portion of an inner angled surface provided by the flared luer connector; and
the deflector section sloping across the longitudinal groove and structured and arranged to deflect a tube head adapter other than the flared luer connector.

46. The medical tubing kit of claim 45, wherein the tube head further provides at least one gripper structured and arranged for gripping by an operator as the luer lock fitting is engaged with a syringe.

47. The medical tubing kit of claim 45, wherein the circumferential cone elevates the luer lock fitting away from a surface when the tube head adapter is disconnected from the syringe and at least partially disposed horizontally upon a surface.

48. The medical tubing kit of claim 45, wherein the tube head adapter is generally cylindrical.

49. The medical tubing kit of claim 45, wherein a transition zone between the receiver section and the deflector section is radially offset from the longitudinal groove.

50. The medical tubing kit of claim 45, wherein the circumferential cone has a generally circular cross section normal to the head adapter.

51. The medical tubing kit of claim 45, wherein the angle of the inner angled surface of the circumferential cone is constant.

52. The medical tubing kit of claim 45, wherein the angle of the inner angled surface of the circumferential cone corresponds to a parabola.

53. The medical tubing kit of claim 45, wherein the base is an insert structured and arranged to couple with a base housing.

54. The medical tubing kit of claim 45, wherein the receiver section has a generally circular cross section normal to the longitudinal groove.

55. The medical tubing kit of claim 45, wherein the angle of the receiver section is constant.

56. The medical tubing kit of claim 45, wherein the angle of the receiver section corresponds to a parabola.

57. A method for using flared luer medical tubing, comprising:

providing a tubing having a tube head adapter formed of a resilient material providing a luer lock fitting structured and arranged to engage a syringe, and a circumferential cone rising from the tube head adapter and flaring away from the luer lock fitting, the circumferential cone having an inner angled surface structured and arranged to engage a correspondingly angled receiver section of a base;

engaging the luer lock fitting of the tubing to a syringe having a barrel with a plunger disposed within and movable along the barrel, the circumferential cone thus flaring away from the syringe; and disposing the syringe with engaged tubing within a pump having an actuator and a base, the base having:
a longitudinal groove structured and arranged to receive at least a portion of the tubing;
a receiver section extending away from the longitudinal groove and correspondingly angled to receive at least a portion of the inner angled surface of the circumferential cone; and
a deflector section sloping across the longitudinal groove;
wherein the actuator is structured and arranged to engage the plunger of the syringe and drive the plunger towards the tubing, the force of the actuator further engaging the inner angled surface of the circumferential cone to the receiver section of the base.

58. The method of claim 57, wherein the tube head adapter further provides at least one gripper structured and arranged for gripping by an operator as the luer lock fitting is engaged with a syringe.

59. The method of claim 57, wherein the circumferential cone elevates the luer lock fitting away from a surface when the tube head adapter is disconnected from the syringe and at least partially disposed horizontally upon a surface.

60. The method of claim 57, wherein the circumferential cone has a generally circular cross section normal to the head adapter.

61. The method of claim 57, wherein the angle of the inner angled surface is constant.

62. The method of claim 57, wherein the angle of the inner angled surface corresponds to a parabola.

63. The method of claim 57, wherein a transition zone between the receiver section and the deflector section is radially offset from the longitudinal groove.

64. The method of claim 57, wherein the base is a component of a syringe pump.

65. The method of claim 57, wherein the base is an insert structured and arranged to couple with a base housing.

66. The method of claim 57, wherein the receiver section has a generally circular cross section normal to the longitudinal groove.

67. The method of claim 57, wherein the angle of the receiver section is constant.

68. The method of claim 57, wherein the angle of the receiver section corresponds to a parabola.

* * * * *